(12) United States Patent
Izrailit

(10) Patent No.: US 10,433,440 B2
(45) Date of Patent: Oct. 1, 2019

(54) POWER SUPPLY UNIT

(71) Applicant: Tetra Laval Holdings & Finance S.A., Pully (CH)

(72) Inventor: Iosif Izrailit, Newton, MA (US)

(73) Assignee: TETRA LAVAL HOLDINGS & FINANCE S.A., Pully (CH)

( * ) Notice: Subject to any disclaimer, the term of this patent is extended or adjusted under 35 U.S.C. 154(b) by 511 days.

(21) Appl. No.: 15/119,932

(22) PCT Filed: Jan. 21, 2015

(86) PCT No.: PCT/EP2015/051064
§ 371 (c)(1),
(2) Date: Aug. 18, 2016

(87) PCT Pub. No.: WO2015/124353
PCT Pub. Date: Aug. 27, 2015

(65) Prior Publication Data
US 2017/0064853 A1  Mar. 2, 2017

(30) Foreign Application Priority Data
Feb. 19, 2014 (SE) ..................... 1450196

(51) Int. Cl.
*H05K 5/02* (2006.01)
*H02M 7/10* (2006.01)
*A61L 2/08* (2006.01)

(52) U.S. Cl.
CPC ............ *H05K 5/0247* (2013.01); *A61L 2/087* (2013.01); *H02M 7/106* (2013.01); *A61L 2202/23* (2013.01)

(58) Field of Classification Search
CPC ........ A61L 2/08; A61L 2/087; A61L 2202/23; H02M 7/106; H05K 5/0247
See application file for complete search history.

(56) References Cited

U.S. PATENT DOCUMENTS 3,063,000 A  11/1962  Cleland
3,253,646 A * 5/1966  Koltuniak ............... H01F 27/08
165/104.34

(Continued)

FOREIGN PATENT DOCUMENTS

CN  202307379 U  7/2012
DE  976500 C  10/1963
(Continued)

OTHER PUBLICATIONS

A U.S. application filed on Aug. 18, 2016 entitled "Power Supply Unit", naming Iosif Izrailit as the inventor.
(Continued)

*Primary Examiner* — David E Smith
(74) *Attorney, Agent, or Firm* — Buchanan Ingersoll & Rooney PC

(57) ABSTRACT

Power supply unit, in particular for a sterilization device, comprising a housing, an electric system and an electric insulation system, wherein the electric insulation system comprises at least one insulation shield, wherein the electric system is located within the housing, and wherein the electric system has, during operation, zones that have different voltage distributions, wherein the housing comprises a plurality of areas, and wherein at least one area comprises the at least one insulation shield, wherein those areas which distance to a zone of the electric system which voltage distribution exceeds a first voltage threshold is below a minimum distance comprise at least one insulation shield.

13 Claims, 7 Drawing Sheets

(56) References Cited

U.S. PATENT DOCUMENTS

Figure 1:
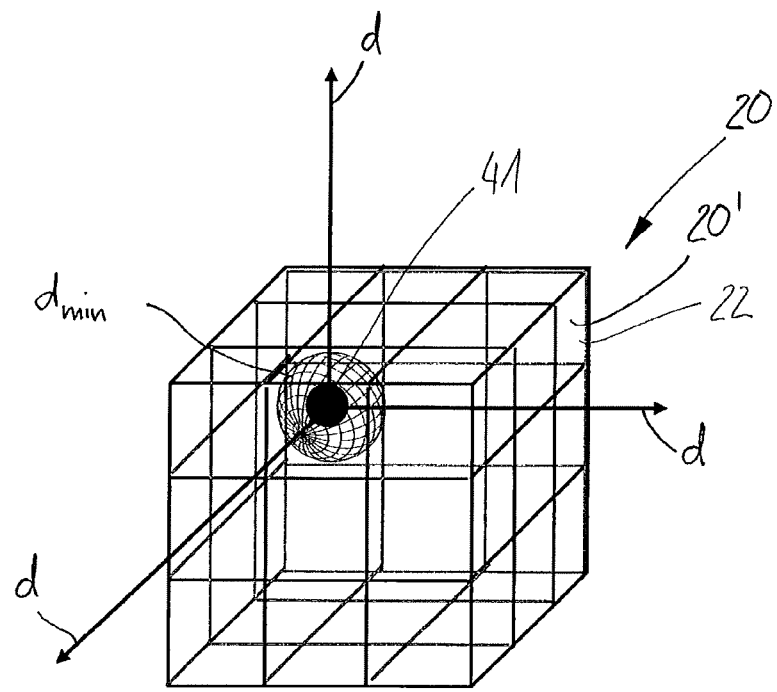
Figure 1:
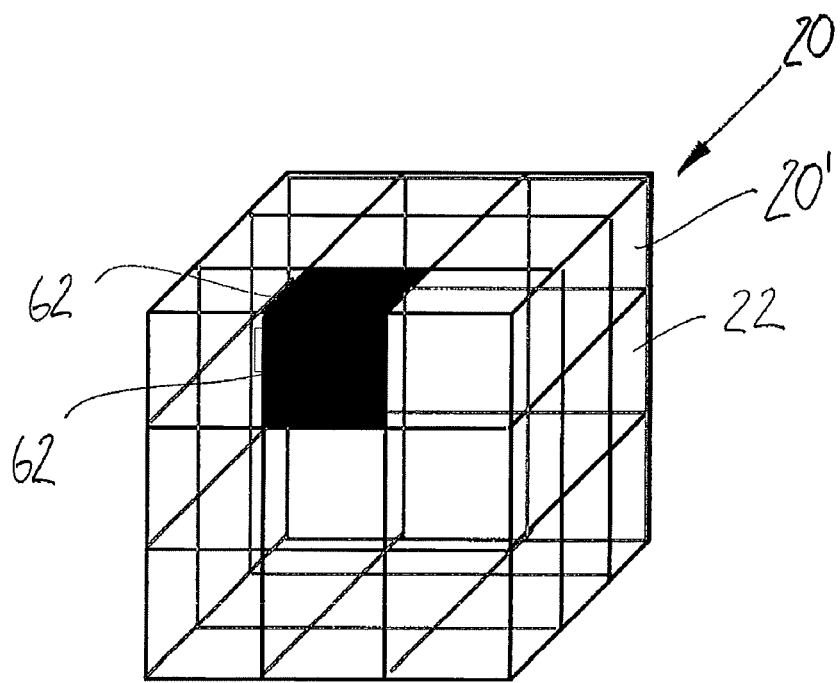

| | | | |
|---|---|---|---|
| 3,544,707 A | 12/1970 | Gamble | |
| 2008/0073549 A1* | 3/2008 | Avnery | B65B 55/08 250/397 |
| 2008/0203366 A1* | 8/2008 | Blackburn | C08J 5/18 252/609 |
| 2011/0012032 A1* | 1/2011 | Bufano | A61L 2/087 250/492.3 |
| 2011/0084221 A1* | 4/2011 | Eguchi | A23L 3/26 250/492.3 |
| 2011/0242853 A1* | 10/2011 | Agarwal | H02M 3/337 363/16 |
| 2017/0056539 A1 | 3/2017 | Mellbin | |
| 2017/0064878 A1 | 3/2017 | Izrailit | |
| 2017/0065734 A1 | 3/2017 | Izrailit | |
| 2017/0065735 A1 | 3/2017 | Mellbin | |

FOREIGN PATENT DOCUMENTS

| | | | |
|---|---|---|---|
| FR | 2 239 040 A1 | 2/1975 | |
| JP | S49-104184 A | 10/1974 | |
| JP | S59-129388 U | 8/1984 | |
| JP | 7-230326 A | 8/1995 | |
| JP | 07230326 A | * 8/1995 | |
| JP | H11-281798 A | 10/1999 | |
| JP | 2013-042580 A | 2/2013 | |

OTHER PUBLICATIONS

A U.S. application filed on Aug. 18, 2016 entitled "Power Supply Unit", naming Håkan Mellbin as the inventor.
A U.S. application filed on Aug. 18, 2016 entitled "Power Supply Unit", naming Oosif Izrailit as the inventor.
International Search Report (PCT/ISA/210) dated Sep. 25, 2015, by the European Patent Office as the International Searching Authority for International Application No. PCT/EP2015/051064.
Written Opinion (PCT/ISA/237) dated Sep. 25, 2015, by the European Patent Office as the International Searching Authority for International Application No. PCT/EP2015/051064.
Office Action dated Sep. 5, 2014 by the Swedish Patent Office in counterpart Swedish Application No. 1450196-9.
Office Action (Notification of Reasons for Refusal) dated Nov. 6, 2018, by the Japanese Patent Office in corresponding Japanese Patent Application No. 2016-552896, and an English Translation of the Office Action. (9 pages).

* cited by examiner

POWER SUPPLY UNIT

This invention relates to a power supply unit, in particular for a sterilization device, to a sterilization device, in particular for packaging material and to a method to electrically insulate a power supply unit, in particular for a sterilization device.

Electron beam irradiation has been considered as a promising alternative for sterilizing purposes for which wet chemistry involving hydrogen peroxide has been the traditional technical platform. Electron beam irradiation provides sufficient sterilization of e.g. packaging material eliminating negative consequences of wet chemistry within e.g. a packaging machine. In this context, power supply units are necessary to provide the high voltage that is used to operate one or more electron beam emitters. However, generating high voltage involves the problem of creating corona and arcs inside the housing of the power supply unit. Known insulation techniques for the housing of the power supply unit are, however, too heavy or require too much raw materials and supplies. In this context, in particular the weight of the power supply unit has to be considered as the power supply units are often arranged at movable mechanisms.

Therefore, there is a desire to provide a power supply unit, in particular for a sterilization device, a sterilization device, in particular for packaging material and a method to electrically insulate a power supply unit, in particular for a sterilization device, which maintains low weight and high cost effectiveness in combination with optimal electric insulation properties.

The invention proposes a power supply unit according to claim 1, by a sterilization device according to claim 12 and by a method to electrically insulate a power supply unit according to claim 13 to meet the desire. Additional advantages and features of preferred embodiments of the current invention are defined in the dependent claims.

According to the invention, a power supply unit, in particular for a sterilization device, comprises a housing, an electric system and an electric insulation system, wherein the electric insulation system comprises at least one insulation shield, wherein the electric system is located within the housing, and wherein the electric system has, during operation, zones that have different voltage distributions, wherein the housing comprises a plurality of areas, and wherein at least one area comprises the at least one insulation shield, characterized in that those areas which distance to a zone of the electric system which voltage distribution exceeds a first voltage threshold is below a minimum distance comprise at least one insulation shield.

In another embodiment a power supply unit for providing a high output voltage is provided. The power supply unit comprises an electric system located inside a housing of the power supply unit. The electric system is divided into several areas. Each area is assigned a voltage distribution value, representing an operating voltage of components located in said area. A first area of those several areas, whose distance to a second area of those several areas, whose voltage distribution value exceeds a first voltage threshold is below a pre-specified distance comprises at least one insulation shield.

In an embodiment of the present invention, the at least one insulation shield can at least partly be located between the first and second area.

The power supply unit is connectable or connected, respectively, to an electron beam emitter or to a plurality of electron beam emitters, for example 2, 3, 4, 5, 6 7, 8, 9, 10, 11, 12 and more. The combination of a power supply unit with at least one electron beam emitter is named sterilization device. Generally, the connection is a form and/or force fit connection.

The electron beam emitter comprises an electron generator for emitting charge carriers, such as electrons, along a path, the electron generator is generally enclosed in a hermetically sealed vacuum chamber. The vacuum chamber is provided with an electron exit window. Furthermore, the electron generator comprises a cathode housing and a filament. In use, an electron beam is generated by heating the filament. When an electrical current is set through the filament, the electrical resistance of the filament causes the filament to be heated to a temperature in the order of 2.000° C. This heating causes the filament to emit a cloud of electrons. The electrons are accelerated towards the electron exit window by means of a high potential difference between the cathode housing and the electron exit window. Subsequently, the electrons pass through the electron exit window and continue towards a target area, e.g. a part of a packaging material that has to be sterilized. The high potential difference is created by connecting the cathode housing and the filament to the power supply unit providing said high potential, while connecting the vacuum chamber to ground potential. The difference between the two potential is given the voltage accelerating the electrons. One can also say, said voltage is supplied by the power supply unit. The voltage lies, according to one or more embodiments, in the range of about 80 to 150 kV. However, higher and lower values are also possible.

An electron beam emitter as described before can be used for sterilization of packaging material, food, biological or medical devices etc. There are no limitations concerning the content of the packaging material, it may comprise web based material, carton blanks, performs of any sort or even glass or plastic bottles. The content can be liquid or solid. There are also no limitations concerning the use of the sterilization device or the electron beam emitter itself, respectively. Thus, the electron beam emitter or the sterilization device, respectively, can be used for inside or outside sterilization of e.g. packaging material, such as packaging containers.

An electric connection between the power supply unit and the electron beam emitter is provided by a high voltage output connector of the power supply unit. The high voltage output connector provides a connection to the electric system or to at least one part of the electric system, respectively, inside the housing.

In another embodiment, a special high voltage output connector can be omitted, if the power supply unit and particularly the connection between the power supply unit and the emitter including all wires and connection are properly sealed and the interior of the supply unit is flushed with an insulation gas. To further improve the dielectric strength, a sufficient space in the range of about 20 to 50 mm and particularly bigger than 30 mm should be kept between any cables or supplying the emitter and operating at high voltages and the housing. An hermetic seal is located between the emitter and the housing to maintain the vacuum within the emitter and a pressurized housing.

Generally speaking, the electric system is adapted to generate the high voltage that is used to operate the one or more electron beam emitters. However, if high voltage is generated, electric insulation is an issue. In particular, corona should be avoided.

Corona discharge is an electrical discharge brought on by the ionisation of a medium surrounding a conductor that is electrically energized. The discharge will occur when the strength (potential gradient of the electric field) around the conductor is high enough to form a conductive region, but not high enough to cause electrical breakdown or arcing to nearby objects. However, in the present context also electric arcs or arc discharges have to be avoided as they can damage the sterilization device and all connected components. Additionally, in particular the people that work with the sterilization device or the power supply unit, respectively, have to be sufficiently protected. Therefore, the housing comprises the insulation system that comprises at least one insulation shield.

In this context, it has to be considered that the electric system can comprise a plurality of electric components. These components may be operated in, operate on or otherwise utilise different voltages. For example, some electric components or at least parts of the electric components are adapted to have different voltages or voltage levels (levels of a different potential) which means that they are for example operated with different voltages or which means that they generate different voltages step wise or continuously. It is possible to identify certain components being operated at certain voltage levels. Very often those components are located in a specific areas of the electric system. In other words the electric system can be divided into areas, wherein a voltage value can be assigned to each of those areas.

It goes without saying that low voltages (e.g. voltages lower than 300 V) usually do not cause the above mentioned problems like corona and arcs. As a consequence, these areas of the electric system do not have to be additionally electrically insulated. Consequently, a first voltage threshold is provided which enables the setting of a lower limit, upon exceeding it, an insulation may become necessary. If the first voltage threshold is exceeded for a given area, the location of said area within the housing has to be taken into consideration. If a distance between said area and another area, located within the housing, exceeds a certain minimum value corona and arc discharges will possibly not occur.

Thus, it has to be checked if the area that exceeds the at least first voltage threshold lies within a minimum distance to the other areas within the housing. If this is the case those other areas shall comprise an insulation shield to prevent corona or arcs from being generated. Alternatively an insulation shield may be arranged between the area exceeding the first voltage threshold and the other area.

In an embodiment, the housing comprises the plurality of areas. In other words, the housing is defined by or divided into the plurality of areas. This division or definition is just theoretically performed. Thus, there are no size limitations for the forms or sizes of the areas. They can be infinitesimally small. Generally, they should be small enough to enable a sufficiently fine distribution or zoning of the housing, but big enough to be practically feasible. Particularly they should have a size sufficient to place an insulation shield and components within said area. Generally, the areas may be defined by the components located in said area, whereby the components are operated by the same or similar voltages.

In accordance with an embodiment, the different areas or parts of the housing, that are located within a minimum distance to a zone of the electric system or to zones of the electric system that exceed (at least) a first voltage threshold, comprise the insulation shield or at least one insulation shield. This means that only those parts or areas of the housing are provided with the insulation shield which require an insulation shield. It goes without saying that the above named features enable a significant cost and weight reduction of the power supply unit.

Expediently, the housing comprises at least one wall, wherein the at least one insulation shield is arranged at and/or in the at least one wall. Consequently, the wall or the at least one wall is defined or divided by the plurality of areas. The walls are the plurality of areas or are divided into the areas, respectively, or the areas include the walls. Generally speaking, the areas include components or parts inside the housing that are attached to the housing and at least parts of the walls.

According to one or more embodiments the wall can comprise metal, for example, aluminium, copper or steel. In case a material with good heat conductivity is used, the wall can provide a cooling effect. The wall can also be made of composite material that comprises different materials like plastic, metal, fibre-reinforced material etc. According to one or more embodiments the housing is made of welded stainless steel, wherein a top end of the housing is expediently movable attached and sealed with appropriate o-rings.

Alternatively or in addition, a liquid gasket can be used. An insulation gas can be used within the housing to further improve the insulation effect and reduce the generation of coronas or arc. Insulation gas such as nitrogen or carbon dioxide, in a hermetically sealed housing cannot leak, even if it is pressurized. In another embodiment some of the components of the electric system can be covered by an insulation layer. All these measure taken alone and in combination reduce or even prevent the creation of undesired coronas or arcs.

A detachable top end or in general a detachable part of the housing enables easy maintenance. The at least one insulation shield can be integrated within the wall or/and it can be attached or arranged, respectively, at the wall, in particular at an inner surface of the wall. In particular, if the insulation shield is just attached at an inner side or an inside of the wall no fixed installation is required. Instead, a form-closed connection can be sufficient. In an embodiment, the insulation shield can also be connected via a form and a force fit connection to the wall, for example via suitable connection elements like screw, bolts etc. Generally, an exchangeable installation shield is very advantageous and comfortable as the insulation system can be easily adapted to different voltage thresholds, even ex post or afterwards.

According to one or more embodiments the housing comprises at least one insert, wherein the at least one insulation shield is arranged at and/or in the at least one insert.

According to one or more embodiments the at least one insert is made of insulation material that is preferably adapted to provide electric insulation properties. That has the advantage that an insulation effect that is provided by the insulation shield can be increased. The material of the insert can be for example plastic, in particular a polymer that provides a high breakdown voltage. According to an embodiment the material may comprise at least one of the following materials: polyethylene, epoxy resin, glass, polypropylene, neoprene, Teflon or other polymers, combinations thereof.

The dielectric strength of an insulation material is the maximum electric field that the pure material can withstand under ideal conditions without breaking down, i.e. without experiencing a failure of its insulating properties. The theoretical dielectric strength of a material is an intrinsic property of the bulk material and is dependent on the configuration of the material or the electrodes with which the field is supplied. The intrinsic dielectric strength is measured using pure materials under ideal laboratory conditions. At breakdown, the electric field frees bound electrons. If the applied electric field is sufficiently high, free electrons from background radiation may become accelerated to velocities that can liberate additional electrons during collisions with neutral items or molecules in a process called avalanche breakdown. Breakdown occurs quite abruptly, resulting in the formation of an electrically conductive path and a disruptive discharge through the material. For solid materials, a breakdown event severely degrades, or even destroys, its insulating capability.

Expediently, the insert is a plate or comprises a plurality of plates, respectively. These plates or these insert plates are arranged and/or attached to the wall, in particular to the inner surface of the walls of the housing. In other words, the insert is also a part of the housing and therefore the insert is also divided or defined by the plurality of areas. In other words, the areas include the insert(s) or the inserts comprise the areas. It is very advantageous to form the insert or the inserts, respectively, exchangeable which can simplify the maintenance of the power supply unit.

According to one or more embodiments the at least one insulation shield is formed by an insulation film, in particular a polyethylene film, wherein the at least one insulation shield is formed by at least one layer of insulation film. The material can be the same as described above. Generally, the material of the insulation shield should provide a high dielectric strength.

According to one or more embodiments the dielectric strength of the material used for the insert and/or the insulation shield lies within a range of about 15 to 180 MV/m. For example, the dielectric strength for polyethylene lies within a range of about 17 to 22 MV/m. A field strength at which breakdown occurs depends on the respective geometries of the dielectric (insulator) and the electrodes with which the electric field is applied, as well as the rate of increase at which the electric field is applied. Because dielectric materials usually contain minute defects, the practical dielectric strength will be a fraction of the intrinsic dielectric strength of an ideal, effect-free, material. Therefore, films as the above mentioned polyethylene film tend to exhibit greater dielectric strength than bigger samples of the same material. Therefore, the above mentioned values for the dielectric strength can be considerably increased using an insulation film on the component to be insulated.

According to a preferred embodiment the insulation film has a thickness of about 0.5 to 1 mm, in particular preferred of about 0.7 to 0.9 mm or about 0.8 mm. Advantageously, the insulation film is manufactured by a longitudinal rolling process which minimizes the (already mentioned) defects of the material. Thus, the insulation film has a minimum amount of air bubbles inside. During the rolling process, most of the bubbles are crashed and gas contamination moves outside the film or splits the bubbles to very small bubbles. However, the small bubbles do not grow inside the insulation film as a result of the electric field that is provided during operation of the power supply unit. Another big advantage of the insulation film is its excellent flexibility, in particular for installation purposes. According to one or more embodiments, four to five layers of insulation film are used for an 30-50 kV insulation shield. For a 80-100 kV insulation shield about six to eight layers of insulation film are used.

According to another embodiment the areas within the housing to which voltage distributions are assigned to exceed different voltage thresholds. Consequently, the insulation shields or system arranged in the housing provides different insulation levels according to the different voltage thresholds.

Thus, according to one or more embodiments, more than one voltage threshold is defined. A second voltage threshold, which is higher than the first voltage threshold may be assigned to a second area within the housing. An additional insulation shield with a high dielectric strength is provided to insulate the second area from the first area (to which the first threshold is assigned to) or to any other area. The first area may be in turn insulated by a first insulations shield from any other area, wherein the first insulation shield comprises a lower dielectric strength than the second insulation shield.

According to one or more embodiments side walls of the power supply unit, in particular of a first chamber, are insulated with a 30 to 50 kV insulation shield. Component of the electric system are arranged in said first chamber. A lower part of the housing representing a second chamber, in particular that part of the housing that is connected e.g. to the electron beam emitter, is additionally insulated with a 80 to 100 kV insulation shield. This means that a first voltage threshold lies within a range of about 30 to 50 kV, wherein the second voltage threshold lies within a range of about 80 to 100 kV.

According to one or more embodiments, the insulation level can be adjusted by a number of insulation shields and/or a number of layers of insulation film. Thus, the dielectric strength of one insulation shield can be increased for example by increasing the number of layers that form the insulation shield or by changing the material of the insulation shield. In other words, material can be used that has a higher dielectric strength. However, also the number of the insulation shields itself can be increased without using material with a higher dielectric strength. This means, for example, that a first insulation shield can be arranged in an insert wherein the insert is attached to the wall and wherein between the insert and the wall is a further insulation shield etc.

According to one or more embodiments, the layers are wound along an axis. They can be wound basically perpendicular to the axis or also helically. Advantageously, a plurality of insulation shields is arranged basically perpendicular to the axis.

According to one or more embodiments, the insulation system comprises an insulation cap, wherein the insulation cap is adapted to insulate at least an area of the electric system that exceeds the second voltage threshold. The insulation cap can also be described as insert, however its form is preferably like a cap as the insulation cap is in particular adapted to electrically insulate the high voltage output connector of the power supply unit and the last stages of a voltage multiplier. According to one or more embodiments a material of the insulation cap comprises polyethylene. Incidentally, the same features and advantages as already mentioned in context with the insert apply to the insulation cap and vice versa. It is a big advantage if the insulation cap is formed and/or built exchangeable.

According to one or more embodiments the at least one insulation shield is arranged at and/or in the insulation cap. The insulation cap can be in direct contact with the wall. Alternatively, between the wall and the insulation cap there can be arranged at least one insert. Generally, the insulation cap is a part of the housing and therefore it is also divided and/or defined by the plurality of areas or parts. The insulations cap comprises the areas or the areas include the insulation cap, respectively.

According to a preferred embodiment the electric system comprises at least one voltage multiplier, wherein the at least one voltage multiplier is located in an area having a voltage value assigned to, which exceeds at least the first voltage threshold.

According to one or more embodiments the housing is filled with an insulation medium, in particular an insulation gas, such as nitrogen, carbon dioxide, halogen. Alternatively the housing is sealed and pumped off, thereby a vacuum is created and present in the housing.

Nitrogen is a dielectric gas that is adapted to prevent or rapidly quench electric discharges as it comprises a low chemical activity and does not cause corrosion of electronic components. An advantage of the use of an insulating gas, such as nitrogen, contrary to the usage of e.g. an insulation oil is that a gas cannot leak out and, for example, damage or pollute a material that has to be sterilized. Another big advantage is the low density of a gas contrary to the density of a liquid insulation material, such as oil. As already mentioned, the sterilization devices are in general arranged at carrousels or the like. These carrousels move very fast and have, for example, to be lifted etc. The weight of the sterilization device should therefore be minimized. This weight reduction can advantageously be realized by the usage of an insulation gas, such as nitrogen. To increase the insulation properties of the insulation gas, the insulation gas is, according to one or more embodiments, dried and/or pressurized. The pressure lies preferably in the range of about 2 to 4 bar above the normal atmospheric pressure, in particular in the range of about 2.5 bar above the normal atmospheric pressure. The term dried means any artificial humidity is removed from the insulation gas and rest humidity within the housing is very low.

According to the invention, a sterilization device, in particular for packaging material, is provided, wherein the sterilization device comprises at least one electron beam emitter and a power supply unit, wherein the power supply unit comprises a housing, an electric system and an electric insulation system, wherein the electric insulation system comprises at least one insulation shield, wherein the electric system is located within the housing, and wherein the electric system has, during operation, zones that have different voltage distributions, wherein the housing comprises a plurality of areas, and wherein at least one area comprises the at least one insulation shield, characterized in that those areas which distance to a zone of the electric system which voltage distribution exceeds a first voltage threshold is below a minimum distance comprise at least one insulation shield.

According to the invention a method to electrically insulate a power supply unit is provided, particular for a sterilization device, wherein the power supply unit comprises a housing and an electric system within the housing, and wherein the electric system comprise components with different operating voltage levels. The housing is divided into a plurality of areas. The method comprises to check if components located in an area exceed with their operating voltage a first voltage threshold. If that is the case, a distance of said area to another area with components of a different operating voltage is measured. Those other areas, whose distance to said area of the electric system which operating voltage levels exceeds a first voltage threshold is below a minimum distance are provided with at least one insulation shield.

The features and advantages of the power supply unit according to the invention apply to the sterilization device according to the invention as well as to the method to electrically insulate a power supply unit according to the invention and vice versa.

Additional aspects and features of the current invention are shown in the following description of preferred embodiments of the current invention with reference to the attached drawings. Single features or characteristics of respective embodiments are explicitly allowed to be combined within the scope of the current invention.

Figure 2:
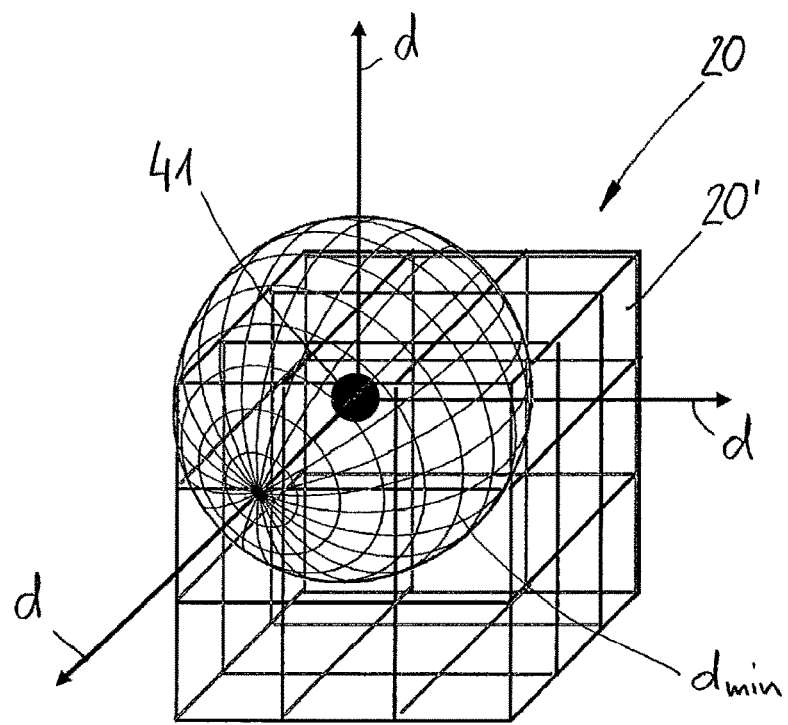
Figure 2:
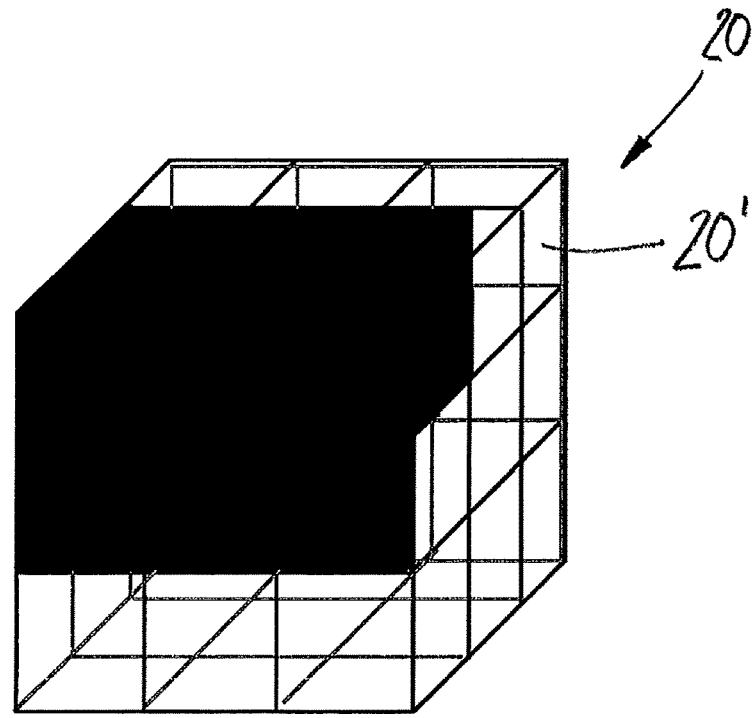
Figure 3:
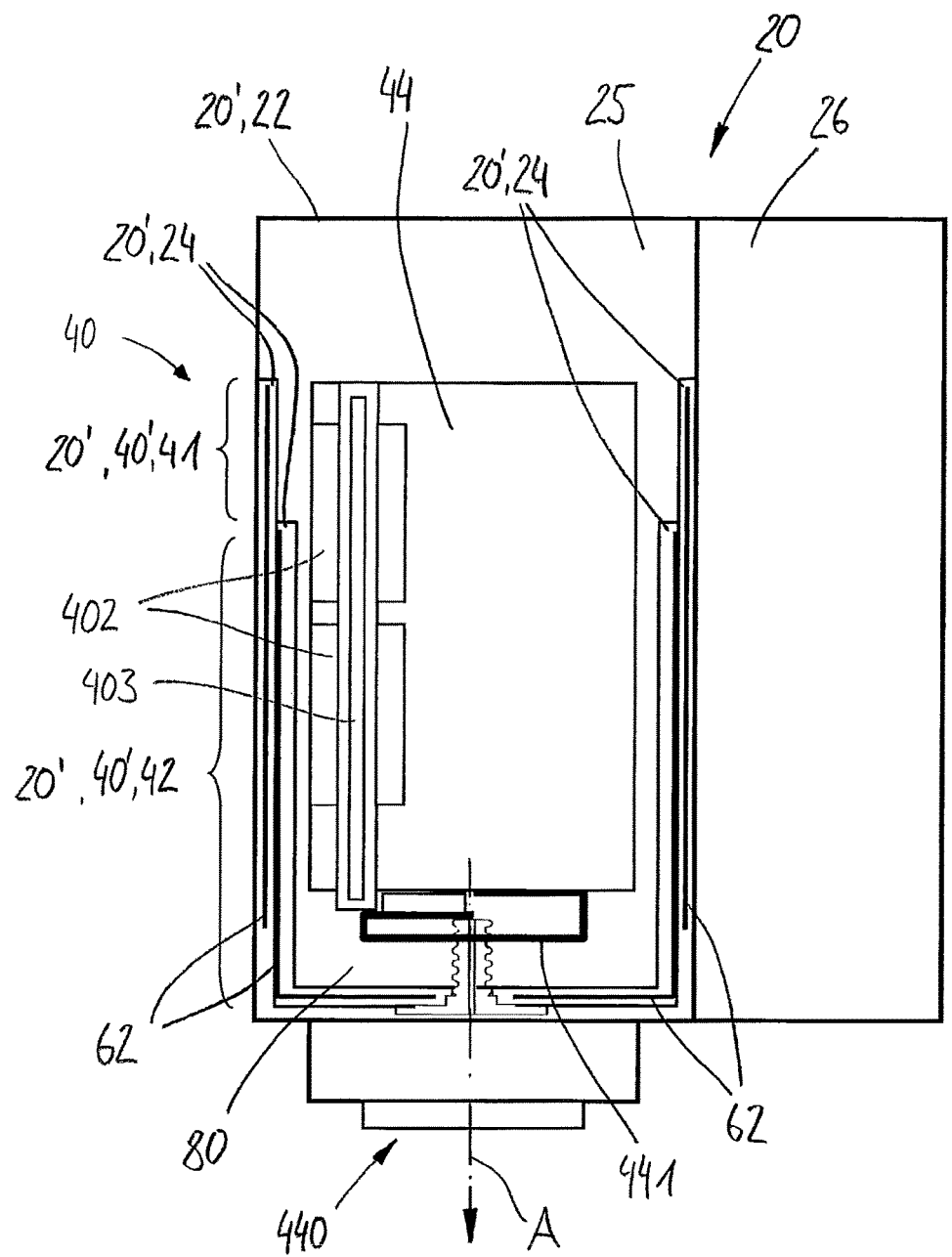
Figure 4A:
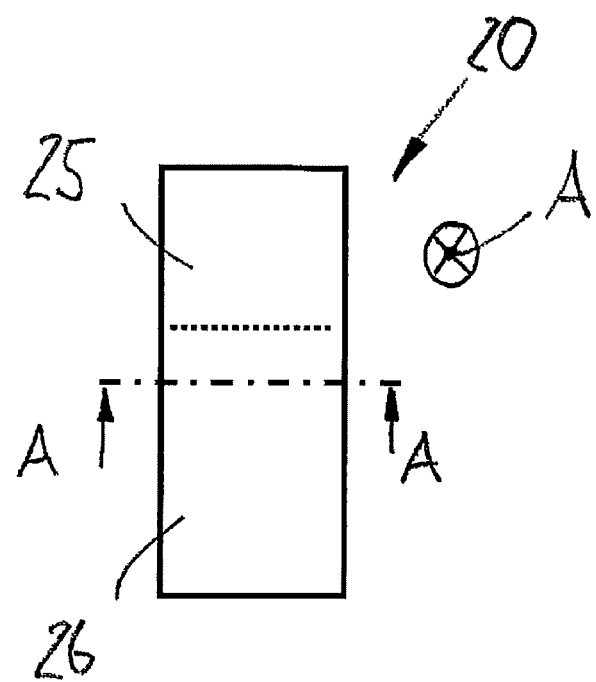
Figure 4B:
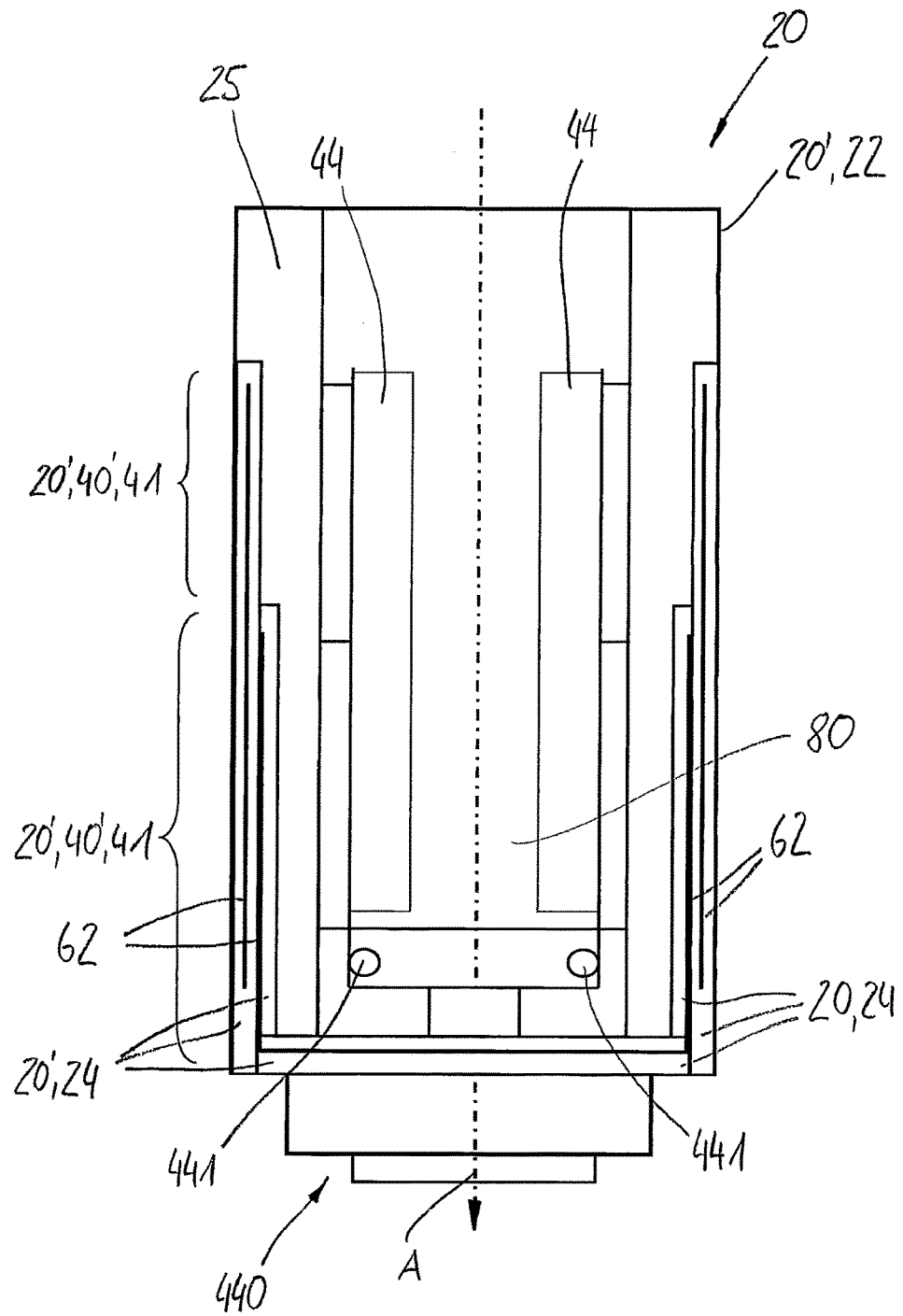
Figure 5:
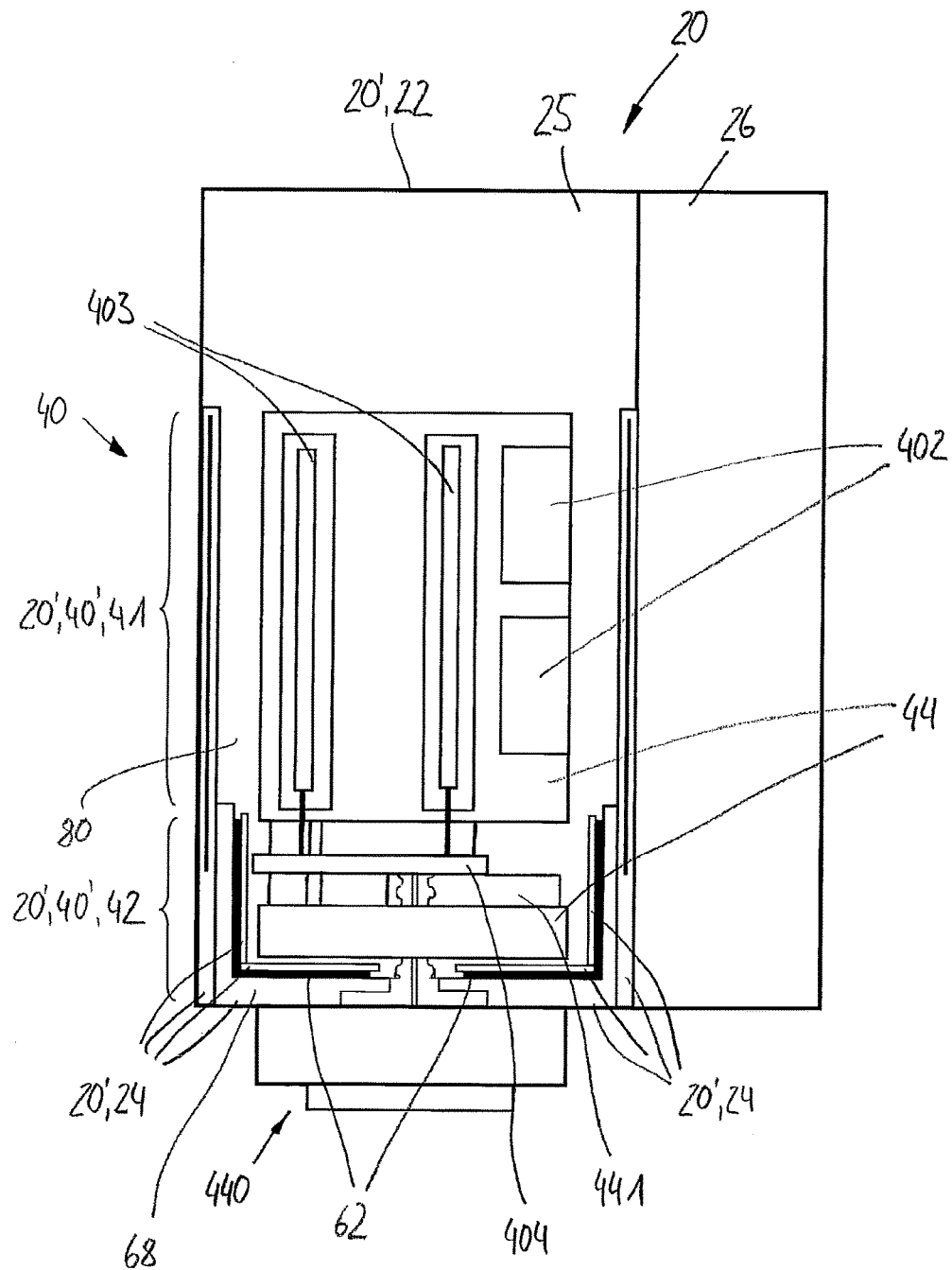
Figure 6:
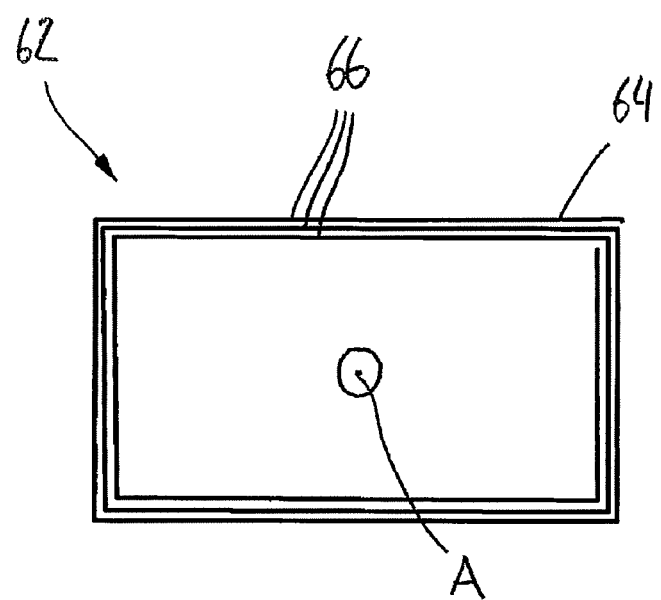
Figure 7:
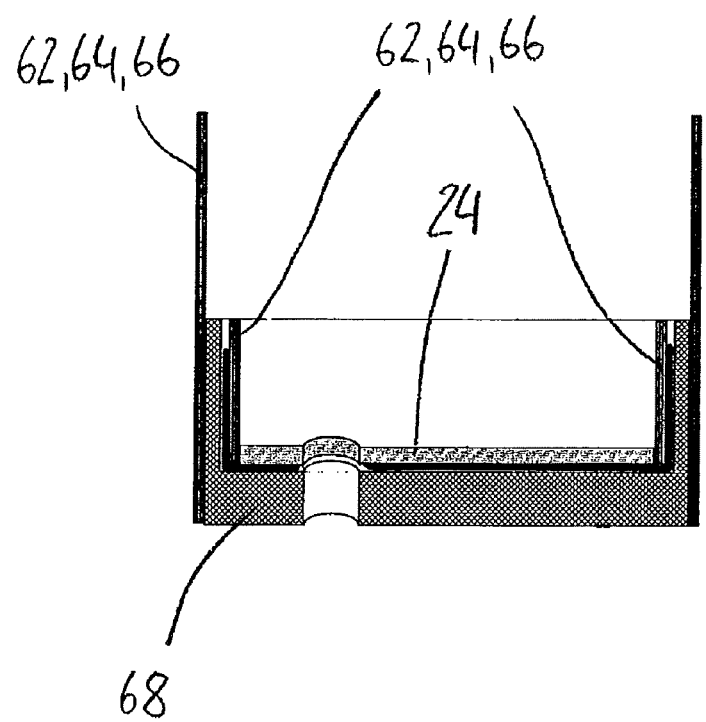

FIG. 1: shows a principle scheme that visualizes the idea of the invention;

FIG. 2: shows a further principle scheme of the idea of the current invention;

FIG. 3: shows a principle diagram of an embodiment of a power supply unit in a side view;

FIG. 4a: shows a top view of the preferred embodiment of the power supply unit shown in FIG. 3;

FIG. 4b: shows an inside of a first chamber of the preferred embodiment of a power supply unit as known from FIG. 3;

FIG. 5: shows a principle diagram of a further embodiment of a power supply unit in a side view;

FIG. 6: shows an insulation film according to one or more embodiments;

FIG. 7: shows an embodiment of an insulation cap in combination with at least one insulation shield.

Referring now to FIG. 1 a principle diagram of a housing 20 having walls 22 is shown. Housing 20 is divided into a plurality of areas 20. Within the housing 20 a zone 41 is located which exceeds a first voltage threshold. Three arrows indicate distances d between the zone 41 that exceeds a first voltage threshold and the housing 20 or the areas 20', respectively.

A sphere that surrounds the zone 41 indicates a minimum distance $d_{min}$ that must not be undergone. This means that the areas 20' of the housing 20 that have a distance d that is smaller than the minimum distance $d_{min}$ have to be provided with at least one insulation shield 62. This is shown in the lower part of FIG. 1, where two of the areas 20' are provided with the insulation shield 62.

The same applies to FIG. 2. The only difference compared to FIG. 1 is that a minimum distance $d_{min}$ is much bigger than that one shown in FIG. 1. As a consequence, the number of areas 20' that have to be provided with an insulation shield 62 is much bigger.

FIG. 3 shows an embodiment of a power supply unit comprising a housing 20 and a first chamber 25 as well as a second chamber 26. The housing 20 is formed by walls 22, wherein the walls 22 comprise a plurality of areas 20'. The division into the plurality of areas 20' is not visualized. The first chamber 25 comprises a voltage multiplier 44, a high voltage measurement divider 403 and filament transformers and rectifiers 402. A high voltage part in the bottom part of the first chamber 25 of the voltage multiplier 44 is protected by a spark current limiter 441. A high voltage output connector 440 which is provided at a bottom end of the housing 20 or the first chamber 25, respectively, is adapted to be connected to an electron beam emitter (not shown).

The above mentioned components form an electric system 40 or are parts of the electric system 40. In this case, the electric system 40 forms generally two zones 40', wherein a first zone 41 that exceeds a first voltage threshold is insulated by an insert 24 that is provided with an insulation shield 62. Preferably, the insulation shield 62 is a 25 to 40 kV insulation shield. A second zone 42 that exceeds a second voltage threshold is insulated by a further insert 24 and a further insulation shield 62 that is arranged in the insert 24 or between the first and the second insert 24, respectively. This insulation shield 62 is preferably an 85 to 100 kV insulation shield. In general, the electric system 40 comprises power electronic components, high voltage components and control system components. According to one or more embodiments the power electronic components are located within the second chamber 26. The same applies to the control system components. Preferably, the high voltage components are arranged within the first chamber 25, wherein the first chamber 25 and the second chamber 26 are both filled with insulation medium 80, in particular insulation gas, such as nitrogen. According to a preferred embodiment the insulations gas is also dried and pressurized, e.g. up to 2.5 or 3 bar above normal pressure.

FIG. 4a shows a top view along the axis A of the power supply unit as shown in FIG. 3. The housing 20 is seen from above, wherein the first chamber 25 and the second chamber 26 are separated by a dotted line. FIG. 4a just shall indicate a sectioning A-A which is explained in FIG. 4b.

FIG. 4b shows the sectioning A-A as explained in FIG. 4a. The sectioning refers to the embodiment shown in FIG. 3. Two voltage multipliers 44 are shown within the first chamber 25. The first chamber 25 is filled with the insulation gas 80, such as nitrogen. The high voltage output connector 440 as well as the spark current limiters 441 are already known from FIG. 3. In this sectioning, the inserts 24 as well as the insulation shields 62 between the housing wall and the electric system within the housing can be seen from a different point of view. However, the arrangement is the same as the one shown in FIG. 3.

FIG. 5 shows a further embodiment of a power supply unit. The power supply unit comprises also a housing 20 that is divided in a first chamber 25 and a second chamber 26. The housing 20 comprises a wall 22 that comprises a plurality of areas 20'. Thus, the main features concerning the housing 20 are the same. However, an electric system 40 is slightly differently arranged. A voltage multiplier 44 comprises two sections that are connected by an interconnection board 404. In other words, the sections are circuit boards, wherein the upper circuit board comprises 4 to 5 multiplier stages that are adapted to multiply an input voltage up to 80 or 90 kV. The lower circuit board comprises preferably two further multiplier stages that are adapted to multiply the voltage form the upper circuit board up to 115 kV or, according to one or more embodiments, even up to 150 kV. Between the lower circuit board of the high voltage multiplier 44 and the interconnection board 404, a spark current limiter 441 is arranged. According to one or more embodiments, the last two stages of the voltage multiplier 44 that are located on the lower circuit board are potted with an electric insulation material. The same applies to the spark current limiter 441. Doing this, the electric insulation properties can be further increased which means that the risk of surface leakage, corona and arc discharges can be further minimized.

The insulation material for potting is preferably epoxy. Epoxy has very good insulation properties and provides very good corona suppression if operating time under electromagnetic field is relatively short. This applies to the spark current limiter 441. Epoxy can be used in applications with relatively low field and low heat dissipation. This applies to the last multiplier stages on the lower circuit board due to the usage of an insulation shield 62. As already known, the housing 20 comprises a high voltage output connector 440 that is adapted for a connection with an electron beam emitter (not shown). Preferably, the housing 20 is filled with an insulation gas 80. The first chamber 25 can be filled as well as the second chamber 26. Similar to the embodiment shown in FIG. 3, the first chamber 25 comprises high voltage measurement dividers 403 and filament transformers and rectifiers 402. A (first) zone 41 of the electric system 40 that exceeds a first voltage threshold is insulated by an insert 24 that comprises an insulation shield 62. This insulations shield 62 is preferably performed as a 30 to 50 kV insulation shield. A (second) zone 42 of the electric system 40 that exceeds a second voltage threshold is electrically insulated by an insulation cap 68 and a further insulation shield 62 that is arranged at the insulation cap 68. As already explained, the (second) zone 42 is mainly formed by the lower circuit board of the voltage multiplier 44 and the spark current limiter 441. Preferably, the insulation shield 62 that insulates the lower circuit board is a 85 to 100 kV insulation shield. The insulation shield 62 that is arranged at the insulation cap 68 is also covered by a further insert 24.

FIG. 6 shows an insulation shield 62 in a view along an axis A. The axis A corresponds to a direction of an axis A as for example shown in FIG. 3. The insulation shield 62 is formed by layers 66 of insulation film 64 that is wound around the axis A. Three layers 66 of insulation film 64 are formed by the insulation film 64.

FIG. 7 shows an embodiment of an insulation cap 68 in combination with at least one insulation shield 62. The insulation cap 68 is surrounded by an insulation shield 62 that is formed by a plurality of layers 66 of insulation film 64. The material of the insulation film 64 is preferably polyethylene. The same applies to an inside insulation shield 62 of the insulation cap 68 that is formed by a plurality of layers 66 of insulation film 64. In addition, the insulation cap 68 is also provided with an insert 24 that is preferably made of polyethylene. The insulation cap 68 is provided with a hole that is adapted to arrange a high voltage output connector (not shown in FIG. 7).

REFERENCE NUMERALS 20 housing
20' area
22 wall (of the housing)
24 insert
25 first chamber
26 second chamber
40 electric system
40' zone
41 zone of an electronic component that exceeds a first voltage threshold
42 zone of an electronic component that exceeds a second voltage threshold
44 voltage multiplier
440 high voltage output connector
441 spark current limiter
402 filament transformer and rectifier
403 high voltage measurement divider
404 interconnection board
62 insulation shield
64 insulation film
66 layer
68 insulation cap
80 insulation medium, insulation gas
A axis
$d_{min}$ distance

The invention claimed is:
1. Method to electrically insulate a power supply unit for a sterilization device, the power supply unit comprising a housing and an electric system,
the electric system being located within the housing,
the electric system having, during operation, zones that have different voltage distributions,
the housing comprising a plurality of areas,
the method comprising:
    checking each of the zones to determine whether each of the zones exceeds a first voltage threshold;
    measuring a distance between each of the zones that exceeds a first voltage threshold and the areas of the housing;
    checking whether and/or which of the distances are below a minimum distance; and
    providing those areas of the housing that are located at a distance below a minimum distance from the zone with at least one insulation shield.

2. Method according to claim 1, wherein the housing comprises at least one wall, and wherein the at least one insulation shield is arranged at and/or in the at least one wall.

3. Method according to claim 1, wherein the housing comprises at least one insert, and wherein the at least one insulation shield is arranged at and/or in the at least one insert.

4. Method according to claim 3, wherein the at least one insert is made of insulation material that provides electric insulation properties.

5. Method according to claim 1, wherein the at least one insulation shield is comprised of an insulation film wherein the at least one insulation shield is comprised of at least one layer of insulation film.

6. Method according to claim 1, wherein the different voltage distributions exceed different voltages thresholds, and wherein the method further comprises adjusting different insulation levels according to the different voltage thresholds.

7. Method according to claim 6, wherein the insulation levels are adjusted by a number of insulations shields and/or a number of layers of insulation film.

8. Method according to claim 1, wherein the method further comprises providing an insulation cap, wherein the insulation cap is adapted to insulate at least a zone of the electric system that exceeds a second voltage threshold.

9. Method according to claim 8, wherein at least one insulation shield is arranged at and/or in the insulation cap.

10. Method according to claim 1, wherein the electric system comprises at least one voltage multiplier, wherein the at least one voltage multiplier comprises at least one zone that exceeds the first voltage threshold.

11. Method according to claim 1, wherein the housing is filled with an insulation medium.

12. Method according to claim 1, wherein the housing is filled with a nitrogen insulation gas.

13. Method according to claim 1, further comprising not providing the insulation shield to areas of the housing that are located at a distance above the minimum distance from the zone.

* * * * *